United States Patent
Abe

(10) Patent No.: US 10,451,560 B2
(45) Date of Patent: Oct. 22, 2019

(54) DAMAGE DETECTION SYSTEM AND DAMAGE DETECTION METHOD

(71) Applicant: SUBARU CORPORATION, Tokyo (JP)

(72) Inventor: Masakatsu Abe, Tokyo (JP)

(73) Assignee: SUBARU CORPORATION, Tokyo (JP)

(*) Notice: Subject to any disclaimer, the term of this patent is extended or adjusted under 35 U.S.C. 154(b) by 0 days.

(21) Appl. No.: 16/257,550

(22) Filed: Jan. 25, 2019

(65) Prior Publication Data

US 2019/0170656 A1 Jun. 6, 2019

Related U.S. Application Data

(63) Continuation of application No. PCT/JP2017/016643, filed on Apr. 26, 2017.

(30) Foreign Application Priority Data

Sep. 7, 2016 (JP) ................. 2016-174377

(51) Int. Cl.
*G01N 21/88* (2006.01)

(52) U.S. Cl.
CPC .. *G01N 21/8806* (2013.01); *G01N 2021/8845* (2013.01); *G01N 2201/088* (2013.01)

(58) Field of Classification Search
CPC ....... G01N 21/8806; G01N 2021/8845; G01N 2201/088
USPC ...................... 356/237.1–237.6, 239.1–239.8
See application file for complete search history.

(56) References Cited

U.S. PATENT DOCUMENTS

| | | | |
|---|---|---|---|
| 5,684,899 A | 11/1997 | Ota | |
| 2004/0247193 A1* | 12/2004 | Qualtrough | B07C 5/3422 382/243 |
| 2005/0163414 A1 | 7/2005 | Takeya et al. | |
| 2011/0025620 A1 | 2/2011 | Jakobsen et al. | |

(Continued)

FOREIGN PATENT DOCUMENTS

| | | |
|---|---|---|
| CN | 102519968 A | 6/2012 |
| JP | H06-177841 | 6/1994 |
| JP | H09-273906 | 10/1997 |

(Continued)

OTHER PUBLICATIONS

International Search Report for PCT/JP2017/016643 dated Jul. 4, 2017 in English and Japanese Language (5 pages inclusive of English machine translation).

(Continued)

*Primary Examiner* — Tri T Ton

(74) *Attorney, Agent, or Firm* — Smith, Gambrell & Russell, LLP

(57) ABSTRACT

According to one implementation, a damage detection system includes optical paths, a light source, a photodetector, and a signal processing system, a signal processing system. The optical paths propagate lights in at least three different directions. The optical paths have at least two paths per one direction. The light source makes the lights incident on one ends of the optical paths respectively. The photodetector detects the lights output from other ends of the optical paths. The signal processing system specifies at least one location of damage based on optical detection signals detected by the photodetector.

10 Claims, 3 Drawing Sheets

(56) References Cited

U.S. PATENT DOCUMENTS

2015/0230730 A1    8/2015    Sabczynski et al.

FOREIGN PATENT DOCUMENTS

| | | |
|---|---|---|
| JP | H11-258448 | 9/1999 |
| JP | 2005-208000 A | 8/2005 |
| JP | 2005-321223 A | 11/2005 |
| JP | 2011-509468 A | 3/2011 |
| JP | 2011-107278 A | 6/2011 |
| JP | 2013-018074 A | 1/2013 |
| JP | 6405461 B2 | 9/2018 |
| WO | 2018/047405 | 3/2018 |

OTHER PUBLICATIONS

Written Opinion for PCT/JP2017/016643 in Japanese Language (5 pages).
First Japanese Office Action dated Mar. 20, 2018 in Patent Application JP2017-523547 (7 pages inclusive of English machine translation).
Decision to Grant a Patent in Japanese Patent Application No. JP2017-523547 (5 pages inclusive of English Machine Translation).
International Preliminary Report on Patentability dated Mar. 15, 2019 for International Patent Application No. PCT/JP2017/016643 (6 pages in Japanese with English translation).
Chinese Office Action dated Aug. 13, 2019 for CN Patent Application No, 201780046741.5 (7 pages in Chinese with English machine translation).

* cited by examiner

DAMAGE DETECTION SYSTEM AND DAMAGE DETECTION METHOD

CROSS REFERENCES TO RELATED APPLICATIONS

This is a continuation of Application PCT/JP2017/16643, filed on Apr. 26, 2017.

This application is based upon and claims the benefit of priority from Japanese Patent Application No. 2016-174377 filed on Sep. 7, 2016; the entire contents of which are incorporated herein by reference.

FIELD

Implementations described herein relate generally to a damage detection system and a damage detection method.

BACKGROUND

As a nondestructive inspection method for detecting damage, which arose in a structure, with no destruction, a method of using an optical fiber is conventionally known. Moreover, as a concrete example of damage detecting method using an optical fiber, technique that an optical signal is propagated with an optical fiber attached to a structure from which damage should be detected and whether damage arose in the structure is determined by observing change in intensity of the optical signal is known (for example, refer to Japanese Patent Application Publication JP2005-321223 A and Japanese Patent Application Publication JP2005-208000 A).

An object of the present invention is to provide a damage detection system and a damage detecting method which can specify respective positions of damage more exactly even when damage arises at a plurality of positions.

SUMMARY OF THE INVENTION in general, according to one implementation, a damage detection system includes optical paths, a light source, a photodetector, and a signal processing system, a signal processing system. The optical paths propagate lights in at least three different directions. The optical paths have at least two paths per one direction. The light source makes the lights incident on one ends of the optical paths respectively. The photodetector detects the lights output from other ends of the optical paths. The signal processing system specifies at least one location of damage based on optical detection signals detected by the photodetector.

Further, according to one implementation, a damage detection method includes; making lights incident on one ends of optical paths propagating the lights in at least three different directions; detecting the lights output from other ends of the optical paths by a photodetector; and specifying at least one location of damage based on optical detection signals detected by the photodetector. The optical paths have at least two paths per one direction.

DETAILED DESCRIPTION

A damage detection system and a damage detecting method according to implementations of the present invention will be described with reference to the accompanying drawings, (Structure and Function)

Figure 1:
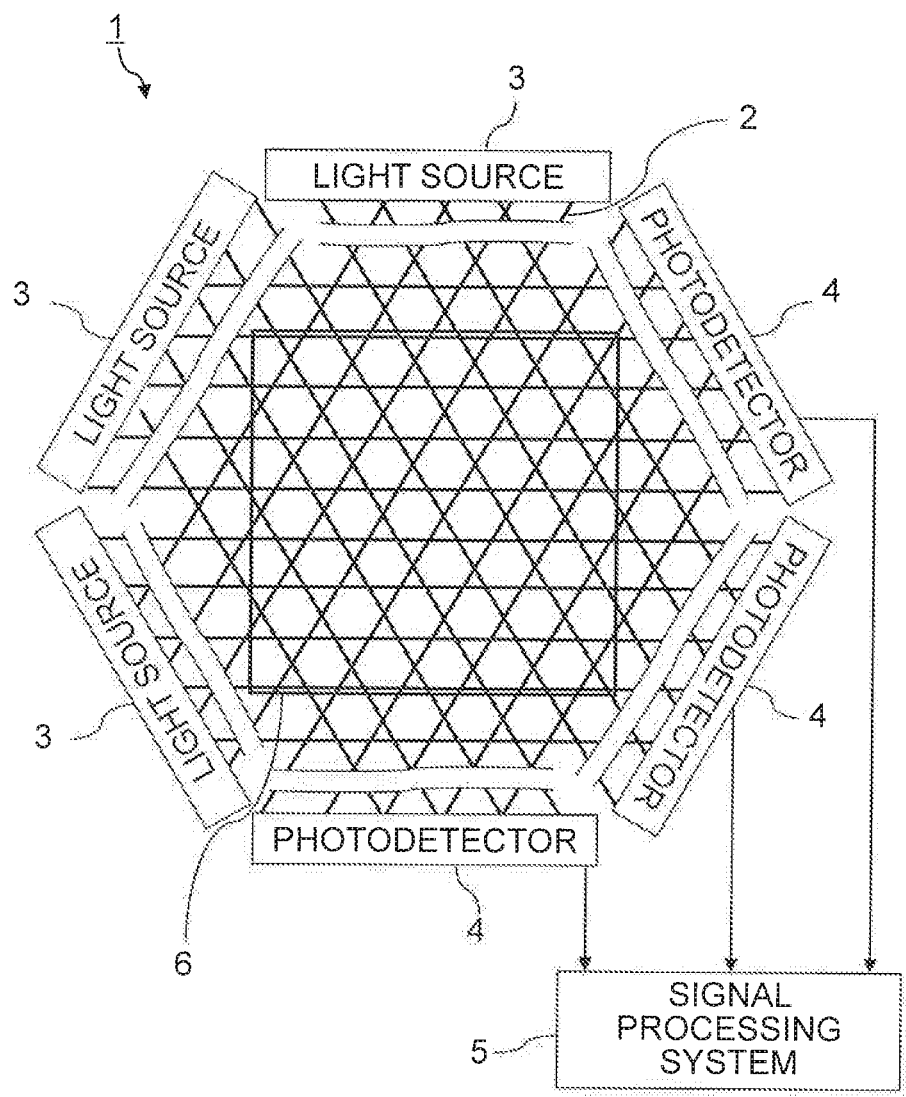
FIG. 1 is a configuration diagram of a damage detection system according to an implementation of the present invention.

FIG. 1 is a configuration diagram of a damage detection system according to an implementation of the present invention.

A damage detection system 1 is a system for specifying each location of damage which arose in a targeted structure. For that purpose, the damage detection system 1 has a plurality of optical paths 2, at least one light source 3, at least one photodetector 4, and a signal processing system 5.

The optical paths 2 are disposed on a surface of a structure object from which damage should be detected. In an example shown in FIG. 1, the optical paths 2 have been disposed on a surface of an aircraft structural object 6, such as a wing structure object, so that a location of damage which arose in the aircraft structural object 6 can be specified.

In particular, the optical paths 2 are disposed so that lights can be propagated in not less than three directions different from each other and at least two optical paths 2 lie in every direction. Therefore, the optical paths 2 are disposed in a lattice shape having not less than three axes. In an example shown in FIG. 1, some parallel optical paths 2 have been disposed per a single direction so that lights can be propagated in three directions.

Examples of optical element for forming each of the optical paths 2 include an optical fiber and an optical waveguide. Note that, an optical fiber is one kind of optical waveguide in the broad sense. Typical examples of a narrowly-defined optical waveguide include an inorganic optical waveguide, such as a glass optical waveguide, and a polymer optical waveguide. A polymer optical waveguide is originally an optical element for a printed circuit board of optical signals, and is also called an organic optical waveguide, a plastic optical waveguide, a polymer optical interconnection, a polymer optical circuit, or the like.

A polymer optical waveguide consists of a cladding layer and a core layer formed inside the cladding layer. The core layer of the polymer optical waveguide can be made of a polymer material while the cladding layer can be made of a resin sheet or the like. Characteristics of a polymer optical waveguide include no light loss in a direction perpendicular to a length direction, ease in processing, capability of density growth, ease in mounting, and the like.

Therefore, using a polymer optical waveguide in order to form each of the optical paths 2 can narrow a pitch of the optical paths 2 compared with a case where an optical fiber is used. More specifically, when a polymer optical waveguide is used in order to form each of the optical paths 2, the optical paths 2 can be disposed in a lattice state having not less than three axes with a pitch or pitches of not more than 1 mm (the order of micrometer). Moreover, propagating lights in a plurality of directions requires to make the optical paths 2 intersect with each other, and thus, using polymer optical waveguides can form the optical paths 2 without overlapping optical waveguides like a case of using optical fibers. Therefore, using polymer optical waveguides in order to form the optical paths 2 makes it possible to avoid concavity and convexity which arise in a case of crossing optical fibers.

Moreover, a polymer optical waveguide can be formed easily as mentioned above. For example, the optical paths 2 can be simply disposed on the surface of the aircraft structural object 6 only by sticking a resin sheet, on which optical waveguides have been formed as the optical paths 2, on the surface of the aircraft structural object 6.

When the optical paths 2 are formed using optical elements, such as polymer optical waveguides or optical fibers, the thicknesses of the optical paths 2 are almost uniform, but become large locally at portions at which the optical paths 2 intersects with each other. When the optical path 2 is thick locally, light which propagates linearly in the optical path 2 may leak in the intersecting optical path 2. When light leaks out to the intersecting optical path 2, light intensity is lost.

Accordingly, it is desirable to dispose the optical paths 2 so that not less than three optical paths 2 do not intersect each other at one position, from a viewpoint of reducing the loss of lights which propagate in the optical paths 2. In an example shown in FIG. 1, the optical paths 2 have been disposed so that two optical paths 2 always intersect each other. Therefore, the optical paths 2 have been disposed in a lattice shape in which triangles are formed among hexagons, in an example shown in FIG. 1. Such arrangement of the optical paths 2 can reduce leaks of lights in the intersecting optical paths 2.

Respective one ends of the optical paths 2 are connected to the light source 3 or the light sources 3. Therefore, lights can be made incident on the respective one ends of the optical paths 2 from the light source 3 or the light sources 3. Meanwhile, the respective other ends of the optical paths 2 are connected to the photodetector 4 or the photodetectors 4. Therefore, lights output from the respective other ends of the optical paths 2 can be detected by the photodetector 4 or the photodetectors 4. The photodetector 4 can be composed of a photo detection element, such as a photo diode, for converting an optical signal into an electric signal.

Each of the optical paths 2 may be connected to the independent light source 3 and the independent photodetector 4. When the number of the optical paths 2 is large, a large number of the light sources 3 and the photodetectors 4 are necessary according to the number of the optical paths 2.

Accordingly, changing a wavelength of light output to the optical paths 2 makes it possible to make the light source 3 and the photodetector 4 common among the optical paths 2. Specifically, the light source 3 can be adapted so that lights having wavelengths different from each other can be made incident on at least two of the optical paths 2. Meanwhile, the lights having the different wavelengths output from the at least two optical paths 2 can be detected by the common photodetector 4. Thereby, even when the number of the optical paths 2 is large, the numbers of the light sources 3 and the photodetectors 4 can be decreased.

When the light source 3 and the photodetector 4 are made in common among some or all of the optical paths 2, the configuration of the damage detection system 1 can be simplified by bundling the end parts of the optical paths 2 to be connected to the light source 3 and the photodetector 4. Each output side of the photodetector 4 or the photodetectors 4 connected to the end parts of the respective optical paths 2 is connected to the signal processing system 5.

The signal processing system 5 has a function to identify a location of damage based on light detection signals detected by the photodetector 4 or the photodetectors 4. When each detection signal of light is converted from an optical signal into an electric signal in the photodetector 4, the location of damage is specified based on electric signals. Therefore, the signal processing system 5 can be built by circuitry, such as an A/D (analog-to-digital) converter and a computer which has read computer program. Necessary processing, such as noise reduction processing and averaging processing, may be performed to each detection signal of light. Various signal processing may be performed not only to an electric signal but to an optical signal. In that case, an optical element necessary for signal processing of an optical signal can be used to compose the signal processing system 5.

As a method for detecting damage in the signal processing system 5, a desired method based on changes of light intensity signals detected in the photodetector 4 or the photodetectors 4 can be adopted. When an object, such as a bird, a hail, or a stone, collides on the surface of the aircraft structural object 6 which is a detection target of damage, for example, and thereby, damage is generated on the surface of the aircraft structural object 6, a light which propagates in each optical path 2 overlapping the damage is interrupted. Alternatively, a light which propagates in each optical path 2 overlapping the damage is interrupted partially, and thereby, the intensity of the light is decreased. That is, a light propagating in each optical path 2 overlapping an area where damage exists is lost.

For this reason, generation of damage is detectable by detecting an intensity change of light, which propagates in each optical path 2, in the signal processing system 5. Each intensity change of light is detectable by threshold processing of a ratio or a difference between an intensity of light transmitted from the light source 3 and an intensity of light detected in the photodetector 4, for example. More specifically, when an intensity of light detected in the photodetector 4 has decreased relatively to an intensity of light transmitted from the light source 3, with exceeding a threshold value, it can be determined that the light has been lost because of damage.

When an intensity waveform of light is detected with securing a sufficient observing period of light, threshold processing may be performed to a ratio or a difference between representative values, such as integral values or the maximum values. The threshold value necessary for the threshold processing can be determined by simulations and/or experiments.

When intensities of lights which propagate in the respective optical paths 2 are observed by at least one photodetector 4, it can be determined that damage lies on each optical path 2 in which the intensity of propagating light has deteriorated. Therefore, when two intensities of lights which propagate in the optical paths 2 which intersect with each other deteriorate, it can be determined that damage has arisen in an area involving the two intersecting optical paths 2. That is, when reductions in intensities of lights output from the optical paths 2, which propagate the lights in two directions different from each other, are detected respectively, a location of damage can be specified.

However, when damage has arose at a plurality of positions on the surface of the aircraft structural object 6, it is difficult to identify the positions of damage correctly only by detecting respective reductions in intensities of lights output from the optical paths 2 which propagate the lights in two different directions.

Figure 2:
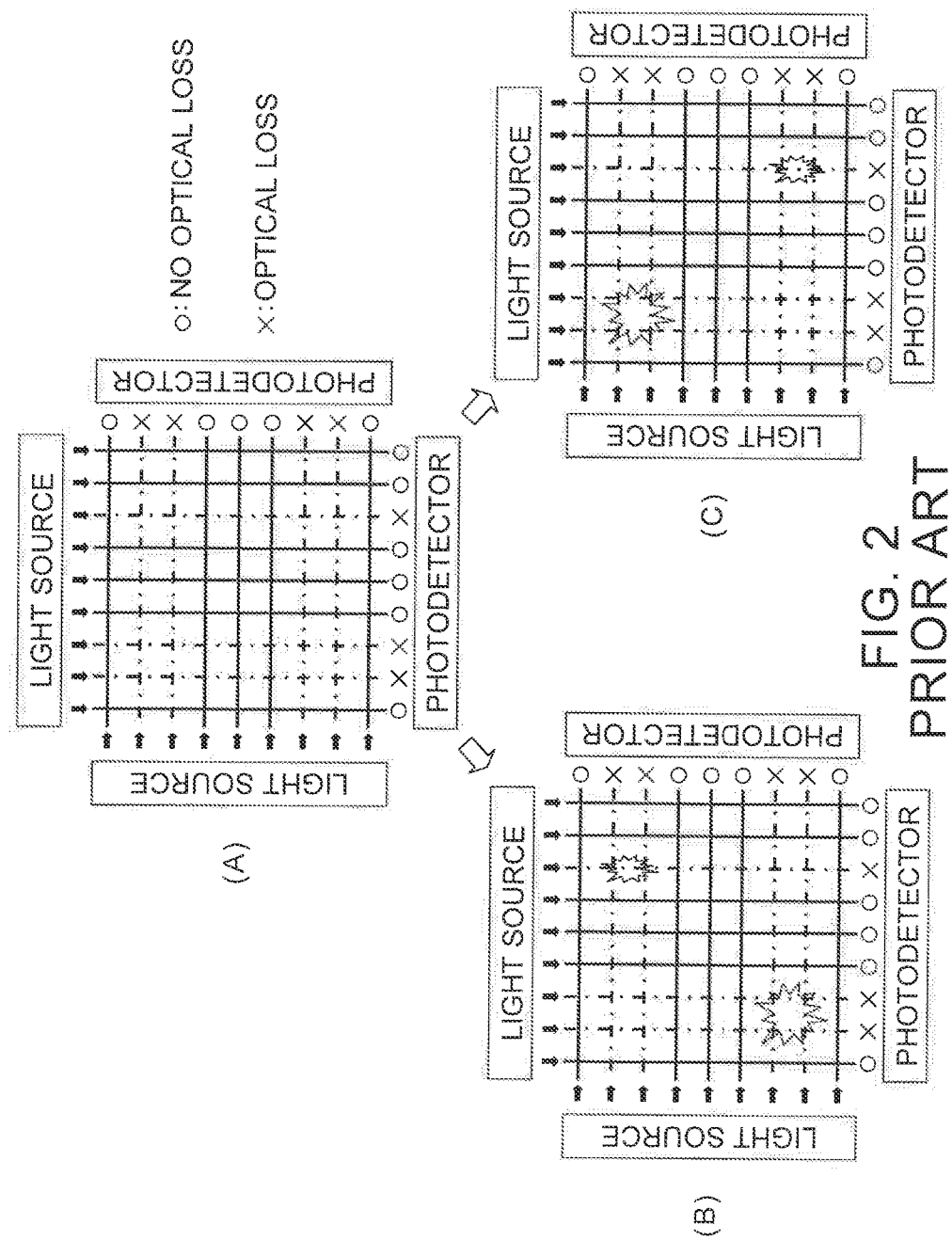
FIG. 2 is a diagram for explaining the problem in a damage detection system of which optical paths have been disposed in a square lattice shape.

FIG. 2 is a diagram for explaining the problem in a damage detection system of which optical paths have been disposed in a square lattice shape.

As shown by (A) in FIG. 2, parallel optical paths can be disposed orthogonally in a square lattice shape and connected to light sources and photodetectors in order to compose a damage detection system. However, when lights propagating in optical paths which are not adjacent in the same direction are lost because of damage as shown by (A) in FIG. 2, for example, the lights are lost at a plurality of intersecting positions of the optical paths. Therefore, the locations of damage cannot be specified. Specifically, when lights are lost as exemplified by (A) in FIG. 2, it cannot be distinguished whether damage arisen at two areas shown by (B) FIG. 2 or at two areas shown by (C) in FIG. 2.

Accordingly, at least one axis can be added to optical paths in a square lattice shape as shown in FIG. 1 so that lights which propagate in not less than three directions can be lost by damage. Then, when respective intensities of lights output from at least three optical paths which respectively propagate the lights in three directions different from each other have decreased, an area including parts of the three optical paths 2 can be specified, as a position at which damage arose, in the signal processing system 5. Thereby, even when damage arose at a plurality of positions in the aircraft structural object 6, each position of damage can be specified. That is, when a plurality of combinations each consisting of three optical paths 2 in which intensities of lights decreased have been found, positions of damage corresponding to the combinations can be specified.

Figure 3:
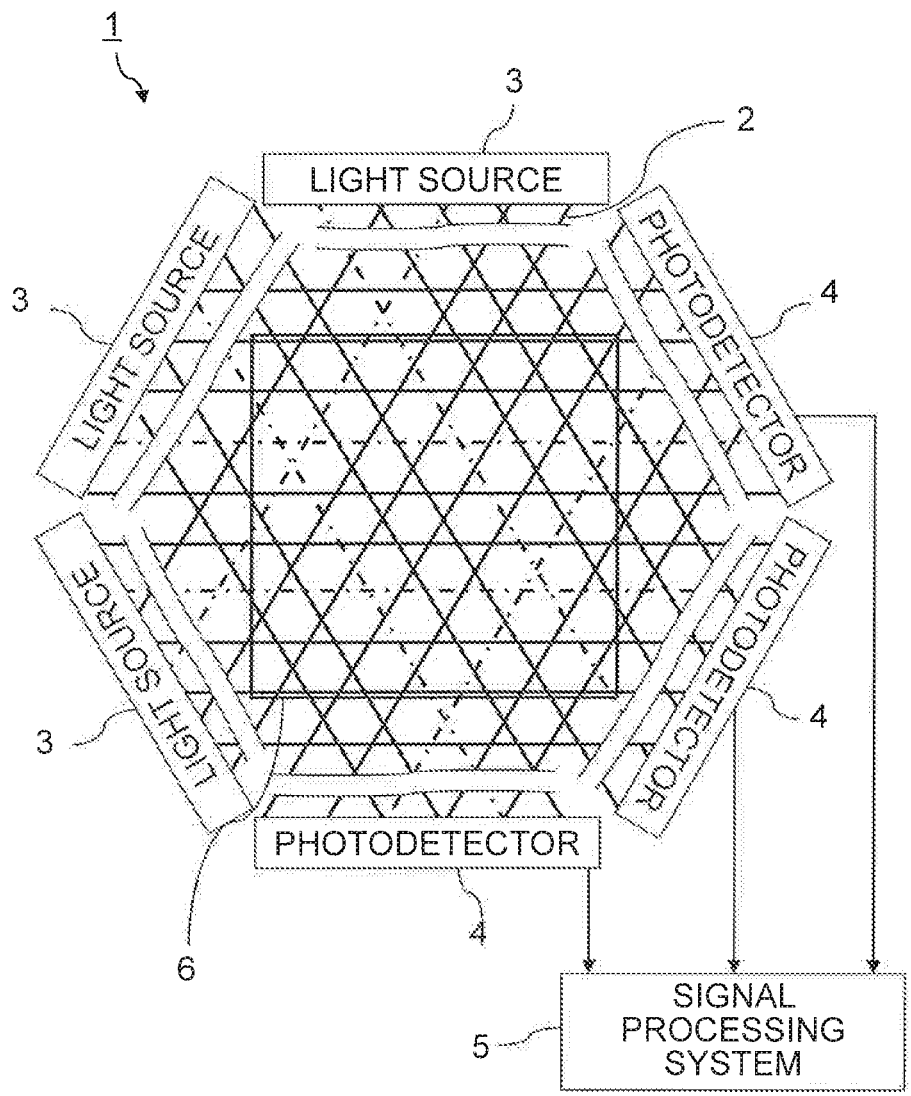
FIG. 3 shows an example of specifying positions of damage by the damage detection system 1 shown in FIG. 1.

FIG. 3 shows an example of specifying positions of damage by the damage detection system 1 shown in FIG. 1.

When damage has arisen at two places of the aircraft structural object 6, lights which propagates in the optical paths 2 shown with the dashed-dotted lines are lost as exemplified in FIG. 3. That is, lights which propagate in three axis directions from each position of damage are lost. Therefore, each area including an intersection of the three optical paths 2 in which propagating lights have been lost can be specified as a damaged area.

When a damaged area is small, lights which propagate in the three optical paths 2 are lost as exemplified in FIG. 3. Therefore, an area where three intersecting positions of the optical path 2, in which lights have been lost, exist adjacently to each other can be specified as an area at which damage arose when the optical paths 2 have been disposed so that the two optical paths 2 necessarily intersect each other as exemplified in FIG. 3.

Meanwhile, when a damaged area is large, the damaged area lies on some parallel optical paths 2 which propagate lights in the same directions. In such a case, an area where a plurality of intersecting positions of the optical paths 2 in which lights have been lost exist adjacently to each other can be also specified as a damaged area. In addition, specifying adjacent intersecting positions out of intersecting positions of the optical paths 2 in which lights have been lost allows detecting a size of damaged area. Further, when a relation between degrees of light loss, e.g., degradation amounts in light intensity, and energies of an impact which caused damage is previously obtained, an energy of an impact which caused damage can be obtained by detecting a degree of light loss.

Note that, what is necessary in order to detect damaged areas which arose at three places is to dispose the optical paths 2 so that lights can propagate in four different directions. Therefore, the optical paths 2 may be disposed not only as examples shown in FIG. 1 and FIG. 3 but so that octagons may be formed. When the optical paths 2 are disposed so that lights can propagate in n directions wherein n is an integer not less than three, it is generally possible to detect damaged areas which arose at up to n−1 places.

Therefore, arrangement of the optical paths 2 can be determined according to the assumed number of damaged areas. Specifically, the optical paths 2 which propagate lights in necessary directions can be disposed so that the required number of damaged positions can be specified. The optical paths 2 may be disposed not only flatly but also spatially. Specifically, the optical paths 2 which propagate lights in not less than three axis directions may be disposed not only two-dimensionally but three-dimensionally. As a matter of course, the optical paths 2 can also be disposed on a curved surface.

As described above, the damage detection system 1 and the damage detection method have the optical paths 2, having not less than three optical axes, to be attached to a desired structural object, such as the aircraft structural object 6, in a lattice shape as a damage detection sensor so that possibly generated damaged locations can be detected respectively by detecting losses of lights propagating in the optical paths 2.

(Effects)

Therefore, even when damaged areas have arisen in a structural object, such as the aircraft structural object 6, because of a crack inside a metal or a composite material, a collision of a bird, a bullet or a hail, or the like, each damaged location can be specified by the damage detection system 1 and the damage detection method. In particular, when the structural object composes an uninhabited airborne vehicle, it becomes possible to detect damage easily during flight. Consequently, detection information of damage can be reflected on flight controls so that excess loads on the aircraft can be reduced during flight. As a result, safety can be improved.

In addition, using an optical waveguide sheet produced by forming the optical paths 2 on a resin sheet allows the optical paths 2 formed at very narrow intervals of about 40 micrometers. It is enough for the aircraft structural object 6 to detect damage in millimeter order. Therefore, damage is detectable with a sufficient position resolution. Further, using an optical waveguide sheet can avoid a leakage of light in a direction perpendicular to the propagating direction of light even in a case of crossing the optical paths 2. Moreover, the damage detection system 1 can be simply attached to a structural object made of a composite material or the like only by sticking an optical waveguide sheet on an outer surface of the structural object without embedding optical fibers or the like inside the structural object.

(Other Implementations)

While certain implementations have been described, these implementations have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A damage detection system comprising:
   optical paths that propagate lights in at least three different directions, the optical paths having at least two paths per one direction, the optical paths being disposed so that not less than three out of the optical paths do not intersect with each other at one position;

a light source that makes the lights incident on one ends of the optical paths respectively;

a photodetector that detects the lights output from other ends of the optical paths; and a signal processing circuitry that specifies at least one location of damage based on optical detection signals detected by the photodetector, an area being specified as the at least one location of the damage when each intensity of at least three lights output from at least three optical paths propagating the at least three lights in the at least three different directions has decreased, the area including each portion of the at least three optical paths, locations of damage corresponding to combinations of the at least three optical paths being specified when the combinations of the at least three optical paths exist.

2. The damage detection system according to claim 1, wherein a polymer optical waveguide is used as each of the optical paths.

3. The damage detection system according to claim 1, wherein the optical paths are disposed, at a pitch of not more than 1 mm, in a lattice shape having not less than three axes.

4. The damage detection system according to claim 1, wherein the light source is adapted to make lights, having wavelengths different from each other, incident on at least two optical paths, and the photodetector is adapted to detect the lights, having the wavelengths different from the each other, output from the at least two optical paths.

5. A damage detection method comprising:

making lights incident on one ends of optical paths propagating the lights in at least three different directions, the optical paths having at least two paths per one direction, the optical paths being disposed so that not less than three out of the optical paths do not intersect with each other at one position;

detecting the lights output from other ends of the optical paths by a photodetector; and specifying at least one location of damage based on optical detection signals detected by the photodetector, an area being specified as the at least one location of the damage when each intensity of at least three lights output from at least three optical paths propagating the at least three lights in the at least three different directions has decreased, the area including each portion of the at least three optical paths, locations of damage corresponding to combinations of the at least three optical paths being specified when the combinations of the at least three optical paths exist.

6. The damage detection method according to claim 5, wherein a resin sheet on which optical waveguides have been formed as the optical paths is stuck on a surface of an aircraft structure and at least one location of damage which arose in the aircraft structure is specified.

7. The damage detection system according to claim 2, wherein the optical paths are disposed, at a pitch of not more than 1 mm, in a lattice shape having not less than three axes.

8. The damage detection system according to claim 2, wherein the light source is adapted to make lights, having wavelengths different from each other, incident on at least two optical paths, and the photodetector is adapted to detect the lights, having the wavelengths different from the each other, output from the at least two optical paths.

9. The damage detection system according to claim 3, wherein the light source is adapted to make lights, having wavelengths different from each other, incident on at least two optical paths, and the photodetector is adapted to detect the lights, having the wavelengths different from the each other, output from the at least two optical paths.

10. The damage detection system according to claim 7, wherein the light source is adapted to make lights, having wavelengths different from each other, incident on at least two optical paths, and the photodetector is adapted to detect the lights, having the wavelengths different from the each other, output from the at least two optical paths.

* * * * *